United States Patent [19]

Fukuoka et al.

[11] Patent Number: 5,223,218

[45] Date of Patent: Jun. 29, 1993

[54] INSTRUMENT FOR QUANTITATIVE ANALYSIS

[75] Inventors: Masayoshi Fukuoka; Akira Matsuyuki, both of Tokyo, Japan

[73] Assignee: Kabushiki Kaisha Meidensha, Tokyo, Japan

[21] Appl. No.: 179,645

[22] Filed: Apr. 8, 1988

[30] Foreign Application Priority Data

Apr. 9, 1987 [JP] Japan .................................. 62-54158
Jun. 25, 1987 [JP] Japan .................................. 62-97630

[51] Int. Cl.⁵ ............................................ G01N 21/76
[52] U.S. Cl. ................................... 422/52; 422/82.05; 356/246; 250/361 C
[58] Field of Search ................... 422/52, 68, 72, 82.05; 356/244, 246; 73/864.23, 864.24, 864.25; 222/363, 366; 436/47; 250/361 C

[56] References Cited

U.S. PATENT DOCUMENTS

| | | | |
|---|---|---|---|
| 3,359,973 | 12/1967 | Hoffman | 422/52 X |
| 3,520,660 | 7/1970 | Webb | 435/8 X |
| 3,756,920 | 9/1973 | Kelbaugh et al. | 422/52 X |
| 3,985,508 | 10/1976 | Williams | 422/65 |
| 4,319,842 | 3/1982 | Priarone et al. | 422/52 X |
| 4,472,352 | 9/1984 | Quesneau et al. | 422/52 |
| 4,755,055 | 7/1988 | Johnson et al. | 422/64 X |

FOREIGN PATENT DOCUMENTS 0071859 2/1983 European Pat. Off. .
7900102 1/1980 PCT Int'l Appl. .
1135091 11/1968 United Kingdom .

OTHER PUBLICATIONS

Use of the Luminescent Bacterial System for the Rapid Assessment of Aquatic Toxicity by A. A. Bulich and D. L. Isenberg, 358 ISA Transactions, vol. 20, (1981) No. 1, Research Triangle Park, N.C., USA pp. 29-33.

Primary Examiner—James C. Housel
Assistant Examiner—Jeffrey R. Snay
Attorney, Agent, or Firm—Bachman & LaPointe

[57] ABSTRACT

An instrument for quantitative analysis includes two shutters, one of which prevents light from being introduced into a black box housing a cell holder from the outside through a port in which a cell may be placed in and taken out the black box, and the other of which prevents light from impinging on a photomultiplier tube which is in communication with the black box. The shutters are controlled by a control unit so that one of the shutters opens when the other closes. The instrument also includes detectors which detect whether or not the cell holder and the cell are disposed at predetermined positions, respectively. The detectors output signals to the control unit. The control unit controls an automatic pipetting device to restrict a sample from being introduced into the cell when both the cell holder and the cell are not disposed at the predetermined position.

8 Claims, 5 Drawing Sheets

INSTRUMENT FOR QUANTITATIVE ANALYSIS

BACKGROUND OF THE INVENTION

1. Field of The Invention

The present invention relates generally to an instrument for quantitative analysis, which monitors light emission occuring due to a chemical reaction between a sample and a reagent(s) for performing quantitative analysis of the sample.

2. Description of The Prior Art

As is well known, various luminescent phenomena, which occur in chemical reactions of chemiluminescent materials, such as a luminol, a lucigenin, an uranine and so forth, with oxidizing agents, have been used for analyses of various unknown materials. In particular, the luminol has been used for analyses of bloodstains since hemoglobin in blood serves as a catalyst in the luminescent reaction of the luminol. The luminol reacts with hydrogen peroxide with the aid of a catalyst, such as potassium ferricyanide and so forth, to cause chemiluminescence. By using this chemiluminescence of the luminol, the hydrogen peroxide content can be determined. Moreover, the luminol reaction can be used for analyses of various metals, such as a cobalt ($Co^{2+}$), a copper ($Cu^{2+}$), a nickel ($Ni^{2+}$), a chromium ($Cr^{3+}$), an iron ($Fe^{2+}$) and so forth. Enzymes, such as a peroxidase and so forth, can effectively function as a catalyst in the reaction of the luminol with the hydrogen peroxide. Therefore, if various materials, such as a protein, a hormone and so forth, are labelled with the enzyme in a similar manner to the EIA (Enzyme Immunoassay) Method, the content of unknown materials can be determined. In addition, it is well known that luciferin, which is a bioluminescent material, reacts with luciferase in the presence of adenosine triphosphate to cause a luminescent phenomenon. By using this phenomenon, the adenosine triphosphate content can be determined.

Figure 7:
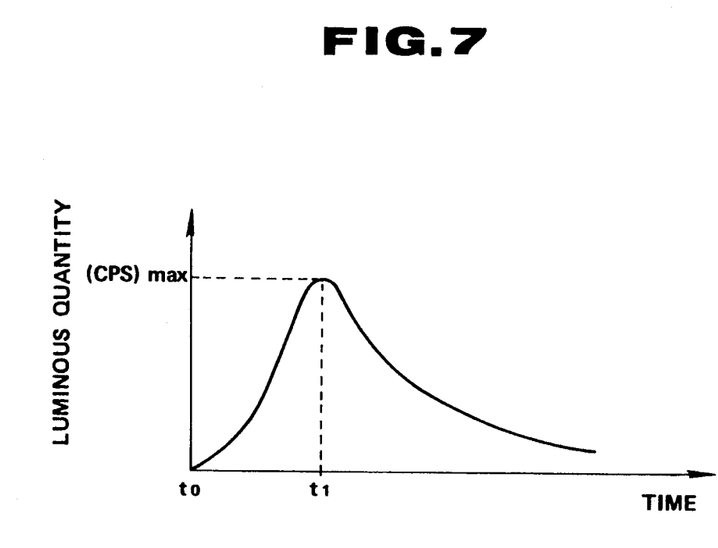
FIG. 7 is a graph of a relationship between time and quantity of light produced in general biochemical luminescent phenomena.

In the aforementioned luminescent phenomena, various luminescent patterns are observed in accordance with concentration or PH of buffer solution including the luminescent material and the catalyst, or the sort of luminescent material, or the mixing ratio of the reagent to the buffer solution. The relationship between time and quantity of emitted light (CPS) in a typical biochemical luminescent phenomenon is shown in FIG. 7. As shown in FIG. 7, as time goes by, the quantity of emitted light (CPS) increases suddenly from a mixing time $t_0$ in which a sample to be determined is mixed with a reagent, reaches the maximum value $(CPS)_{MAX}$ at a time $t_1$, and thereafter decreases gradually. In order to accurately measure the quantity of emitted light shown in FIG. 7, it is necessary to detect the initial quantity of the emitted light $(CPS_{MAX})$ at the time $t_1$ immediately after the sample is mixed with the reagent.

The quantities of the emitted light in the aforementioned luminescent phenomena are generally measured by using the sensor of a photomultiplier tube and so forth, after the sample and the reagent are pipetted into cells or test tubes by means of a manually operable pipette available on the market.

However, according to the aforementioned process in which the pipetting of the sample and reagent is performed by means of the manually operable pipette, it is difficult to measure the initial quantity of the emitted light since the introduction of the materials into the cell requires a lot of time. In particular, in bioluminescent phenomena, the time in which the quantity of emitted light reaches the maximum value is very short. Therefore, in such phenomena, the initial quantity of emitted light can not accurately be measured.

In cases where a very dilute, for example, less than nanomole per liter ($10^{-9}$M) sample is determined by using chemiluminescent materials, the intensity of emitted light is very weak. Therefore, a very small quantity of photons, for example, less than ten photons per second, must be counted. In order to count such a small quantity of photons, it is required to decrease the quantity of unwanted light incident upon the optical sensor of the photomultiplier tube or the like from the outside of the measurement chamber, in which a cell, a cell holder and the optical sensor and so forth are housed, as much as possible. Therefore, the measurement chamber must be enclosed within a tightly covered black box so that no light can be introduced into the chamber from the outside.

In order to accurately count the initial quantity of the light emitted immediately after the sample is mixed with the reagent, and in order to decrease the quantity of the light from the outside of the chamber incident upon the optical sensor, the measurement chamber must comprise a black box, and an automatic pipetting device for injecting the sample and/or the reagent into the cells. The black box is provided with a port for introducing the cell at a location in which the cell introduced into the black box through the port does not obstruct the needles of the automatic pipetting device or Teflon tubes connected to the needles. The cell is horizontally moved from the cell introducing port to an injecting position in which the sample and/or the reagent are to be pipetted into the cell, and thereafter they are injected into the cell and the quantity of emitted light begins to be measured. If such an automatic pipetting device is used, the initial quantity of emitted light (the maximum value) can be measured, even when the quantity of emitted light suddenly changes immediately after the sample is mixed with the reagent. Moreover, by using such a black box, the quantity of light incident upon the optical sensor from the outside of the chamber can be decreased. However, according to this method, it is difficult to prevent light from being introduced into the black box from the outside when the cell is taken in and out the black box. When light introduced into the black box strikes a delicate photoelectric surface of the optical sensor of the photomultiplier tube which is designed to monitor weak light, the photomultiplier tube can become damaged or broken.

Moreover, in the aforementioned instrument for quantitative analysis, the cell and the cell holder can not be accurately arranged at the position in which the sample and/or the reagent are injected into the cell, since the operator can not see into the black box while the cell is moving horizontally into the injecting position. Therefore, the sample and/or the reagent injected into the black box may miss the cell, in which case the cell holder or the inner wall of the black box which are made of metal may be corroded by the sample and/or the reagent. In addition, if the cell is not accurately arranged in the black box, the needle of the pipetting device can not accurately positioned at the injecting position in which the sample and/or the reagent are injected into the cell, so that the sample can not be accurately measured.

Furthermore, when an enzyme is used as a labelling material, the temperature of the reaction system must be constant since the enzyme activity is dependent on the temperature. However, conventional cell holders of instruments for quantitative analysis have no system for maintaining temperature therein. Therefore, the quantity of emitted light measured in the conventional instruments is not a dependable value.

SUMMARY OF THE INVENTION

It is therefore a principal object of the present invention to provide an improved instrument for quantitative analysis, which can accurately measure the quantity of the light produced by injecting a sample and a reagent into a cell.

It is another object of the invention to provide an instrument for quantitative analysis, which can accurately measure the quantity of the light produced by injecting a very small amount of sample and/or reagent into a cell.

It is another object of the invention to provide an instrument for quantitative analysis, which can prevent light from impinging upon the photoelectric surface of an optical sensor when a cell is taken in and out of a black box, so as to protect the optical sensor.

It is another object of the invention to provide an instrument for quantitative analysis, in which a cell and a cell holder supporting the cell can be accurately positioned at the injecting position in which a sample and a reagent are injected into the cell.

It is further object of the invention to provide an instrument for quantitative analysis, which can maintain a selected temperature within the cell.

In order to accomplish the aforementioned and other specific objects, the instrument for quantitative analysis, according to the present invention, includes means for establishing a desired set of operating conditions within the instrument.

According to one aspect of the present invention, the instrument for detecting light produced in a reaction between first and second material for performing quantitative analysis of the first material, comprises:

housing means for defining an optically sealable hollow chamber;

setting means for placing a cell, in which the first material reacts with the second material, at a measuring position within the chamber;

first means for receiving light produced in the reaction when the cell is disposed at the measuring position and for measuring the quantity of the light; and second means for blocking light from impinging on the first means when the cell is disposed at a position other than the measuring position, the second means establishing the optical communication between the cell and the first means and blocking light from being introduced into the chamber when the cell is disposed at the measuring position.

The setting means may comprise carrying means for carrying the cell between the measuring position and a setting position in which the cell is placed in and taken out of the carrying means. The housing means may have an opening through which the cell is placed in and taken out of the carrying means when the cell is disposed at the setting position. The second means may comprise first blocking means for opening the opening when the cell is disposed at the setting position and for closing the opening when the cell is disposed at the measuring position, and second blocking means for blocking the optical communication between the cell and the first means when the cell is disposed at the setting position and for establishing the communication between the cell and the first means when the cell is disposed at the measuring position.

According another aspect of the invention, the instrument for quantitative analysis comprises:

housing means for defining an optically sealable hollow chamber having an opening;

a cell holder, housed in the chamber, for supporting a cell therein, the cell holder being movable between a first position in which the cell is placed in and taken out of the cell holder through the opening, and a second position in which the first material reacts with the second material;

carrying means for carrying the cell holder between the first and second positions;

injection means for injecting the first and second materials into the cell at the second position;

measuring means for measuring the quantity of light produced by the reaction between the first and second materials, the measuring means having a light passage and a light detecting means for detecting light passing through the light passage and impinging thereon;

first protective means, associated with the opening, for blocking light from being introduced into the housing means from the outside thereof, the first protective means being operable between an opened position in which the first protective means fully opens the opening of the housing means in a first operation mode, and a closed position in which the first protective means fully closes the opening in a second operation mode;

second protective means, associated with the light passage of the measuring means, for blocking light from impinging on the light detecting means of the measuring means, the second protective means being operable between an opened position in which the second protective means fully opens the light passage in the second operation mode, and a closed position in which the second protective means fully closes the light passage in the first operation mode;

cell holder detecting means for monitoring the cell holder for producing a first detector signal when the cell holder is disposed at the first position, and a second detector signal when the cell holder is disposed at the second position; and control means for receiving the detector signals produced by the cell holder detecting means for adjusting the first and second protective means, the control means allowing the first and second protective means to operate in the first operation mode when the control means receives the first detector signal, and in the second operation mode when the control means receives the second detector signal.

The cell holder detecting means may include a first switch which is turned on when the communication between the cell holder and the first switch is established in the first position, and a second switch which is turned on when the communication between the cell holder and the second switch is established in the second position. The cell holder detecting means may produce the first signal in response to turning ON of the first switch, and the second signal in response to turning ON of the second switch. The carrying means may comprise a horizontally extending member between the first and second position, so that the cell holder is slidable on the horizontally extending member in a longitudinal direction. The first and second switches respectively may be provided at the ends of the horizontally extending member. The first and second switches respectively may project vertically from the ends of the horizontally extending member, and the cell holder may have first and second recesses on the bottom thereof so that the first and second switches is respectively engageable with the first and second recesses. The first and second switches respectively may be turned on when the first and second switches engage the first and second recesses.

According to another aspect of the invention, the instrument for quantitative analysis comprises:

housing means for defining an optically sealable hollow chamber;

setting means for placing a cell, in which the first material reacts with the second material, at a measuring position in the chamber;

injection means for injecting the first and second materials into the cell at the measuring position;

measuring means for receiving light produced in the reaction when the cell is disposed at the measuring position for measuring the light;

control means, associated with the injection means, for preventing the first and second materials from being injected into the cell when the cell is disposed at a position other than the measuring position, and for allowing the first and second materials from being injected into the cell when the cell is disposed at the measuring position.

The setting means may comprise carrying means for carrying the cell between the measuring position and a setting position in which the cell is placed in and taken out of the carrying means. The instrument may further comprise detecting means for monitoring the cell for outputting a detector signal to the control means at the measuring position, so that the control means allows the first and second materials to be injected into the cell when the control means receives the detector signal. The carrying means may carry a cell holder in which the cell is housed. The detecting means may comprise a first detector for monitoring the cell holder for producing a first detector signal when the cell holder is disposed at the measuring position, and a second detector for monitoring the cell for producing a second detector signal when the cell is disposed at a predetermined position within the cell holder. The control means allows the first and second materials to be injected into the cell when the control means receives the first and second detector signals.

According to another aspect of the invention, the instrument for quantitative analysis comprise:

housing means for defining an optical sealable hollow chamber having an opening;

a cell holder, housed in the chamber, for supporting a cell therein, the cell holder being movable between a first position in which the cell is placed in and taken out of the cell holder through the opening, and a second position in which the first material reacts with the second material;

carrying means for carrying the cell holder between the first and second positions;

injection means for injecting the first and second materials into the cell at the second position;

measuring means for measuring the quantity of light produced by the reaction between the first and second materials;

first detecting means for monitoring the cell holder for producing a first detector signal when the cell holder is disposed at the second position;

second detecting means for monotoring the cell for producing a second detector signal when the cell is housed in the cell holder at a predetermined position; and control means, associated with the injection means, for receiving the first and second detector signals for allowing the injection means to inject the first and second materials into the cell.

The instrument may further comprise a manually operable switch for causing the injection means to inject the first and second materials into the cell when the switch is operated while the control means receives the first and second detector means. The first detecting means may include a switching means which is turned on when the communication between the cell holder and the switching means is established in the second position, so that the first detecting means may produce the first detector signal in response to turning ON of the switching means. The carrying means may comprise a horizontally extending member between the first and second position, so that the cell holder is slidable on the horizontally extending member in a longitudinal direction. Preferably, the switching means projects vertically from the end of the horizontally extending member, and the cell holder has a recess on the bottom thereof, so that the switching means is engageable with the recess. The switching means may be turned on when the switching means engages the recess. The cell holder may comprise a hollow vessel which has a first opening through which the cell may be introduced into the cell holder, and a second opening through which light produced by the reaction between the first and second materials may pass. The cell holder is preferably provided with a pan which supports the cell and has a groove extending in the longitudinal direction, the groove fixing the cell to the pan and allowing light produced in the vicinity of the bottom of the cell to be measured by means of the measuring means. The cell holder may be also provided with means for holding temperature in the cell to be constant. The second opening is preferably covered with a protective cover through which light produced by the reaction between the first and second materials can pass.

According to another aspect of the invention, the instrument for quantitative analysis comprises:

housing means for defining an optically sealable hollow chamber having an opening;

a cell holder, housed in the chamber, for supporting a cell therein, the cell holder being movable between a first position in which the cell is taken in and out of the cell holder through the opening, and a second position in which the first material reacts with the second material;

carrying means for carrying the cell holder between the first and second positions;

injection means for injecting the first and second materials into the cell supported by the cell holder;

measuring means, associated with the housing means, for measuring the quantity of light produced in the reaction between the first and second material in the cell, the measuring means having a light passage and a light detecting means for detecting light passing through the light passage and impinging thereon;

first protective means, associated with the opening, for blocking light from being introduced into the housing means from the outside thereof, the first protective means being operable between an opened position in which the first protective means fully opens the opening in a first operation mode, and a closed position in which the first protective means fully closes the opening in a second operation mode;

second protective means, associated with the measuring means, for blocking light from impinging on the detecting means of the measuring means, the second protective means being operable between an opened position in which the second protective means fully opens the light passage in the second operation mode, and a closed position in which the second protective means fully closes the light passage in the first operation mode;

first detecting means for monitoring the cell holder for producing a first detector signal when the cell holder is disposed at the second position, and a second detector signal when the cell holder is disposed at the second position;

second detecting means for monitoring the cell for producing a third detector signal when the cell is housed in the cell holder; and control means, associated with the first and second protective means, for receiving the detector signals produced by the first detector means for allowing the first and second protective means to operate in the first operation mode when the control means receives the first detector signal, and in the second operation mode when the control means receives the second detector signal, the control means, associated with the injection means, allowing injection means to inject the first and second materials into the cell when the control means receives the second and third detector signals.

BRIEF DESCRIPTION OF THE DRAWINGS

The present invention will be understood more fully from the detailed description given herebelow and from the accompanying drawings of the preferred embodiments of the invention. The drawings are not intended to imply limitation of the invention to this specific embodiment, but are for explanation and understanding only.

In the drawings.

DESCRIPTION OF THE FIRST PREFERRED EMBODIMENT

Figure 1:
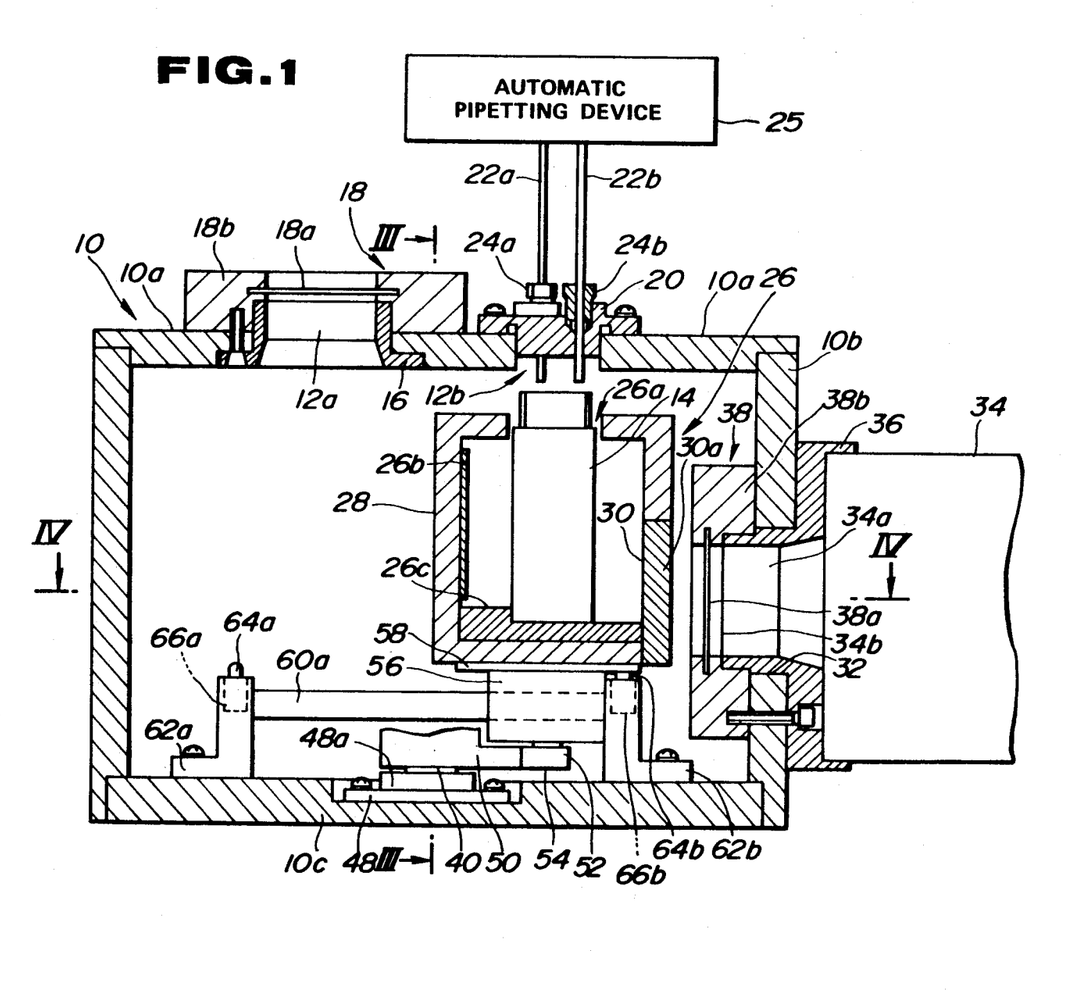
FIG. 1 is a section view of the first and second preferred embodiment of an instrument for quantitative analysis according to the present invention.

Referring now to the drawings, particularly to FIG. 1, the first preferred embodiment of an instrument for quantitative analysis, according to the present invention, includes a black box 10 defining a measurement chamber. The black box 10 is made of metal for example, and can prevent light from being introduced thereto from the outside. The upper wall 10a of the black box 10 has two circular through openings 12a and 12b. A cell 14, in which a sample and a reagent are injected, is taken in and out the black box 10 through the opening 12a, and thus the opening 12a will be referred to as "a cell port". The sample and/or reagent are injected into the cell 14 through the opening 12b, and thus the opening 12b will be referred to as "an injection opening". The cell port 12a is separated from the injection opening 12b by a predetermined distance. A cylindrical flange 16 is inserted into the cell port 12a so that the lower portion thereof is fixed to the inner periphery of the cell port 12a. The upper portion of the cylindrical flange 16 projects upwardly from the upper wall 10a of the black box 10. The inner diameter of the flange 16 is greater than the outer diameter of the cell 14 so that the cell 14 can be taken in and out the black box 10 therethrough. The upper portion of the flange 16 projecting from the upper plate 10a of the black box is covered with an electromagnetic shutter 18 which can automatically open and close the cell port 12a. Well known electric shutters may be used as the shutter 18. According to this embodiment of the invention, the electric shutter can automatically open and close on the basis of a pulse signal produced from a control unit having a microcomputer. The shutter 18 comprises a plurality of vanes 18a overlapping each other, such as a diaphragm, and a shutter mounting member 18b. The vanes 18a are made of plastic so as not to become corroded by the solvents used in chemiluminescent and bioluminescent phenomena. By closing the shutter 18, light introduced into the black box 10 from the outside can be shut out. The injection circumferential portion of which is fixed to the upper wall 10a by means of screws. The lid 20 has two through openings. Teflon tubes 22a and 22b pass through these openings, so that the tips of the tubes 22a and 22b are introduced into the black box 10. A sample to be determined and/or a reagent are injected into the cell 14 in the black box 10 through the Teflon tubes 22a and 22b, respectively. The Teflon tubes 22a and 22b are fixed to the lid 20 by means of set screws 24a and 24b. The other ends of the Teflon tubes 22a and 22b are connected to an automatic pipetting device 25, so that the automatic pipetting device 25 can inject the sample and the reagent into the cell 14 through the Teflon tubes 22a and 22b, respectively. The automatic pipetting device 25 can also inject one of the sample and the reagent into the cell 14 through one of the Teflon tubes 22a and 22b. In this case, the other of the sample and the reagent can be previously injected into the cell 14.

Figure 2:
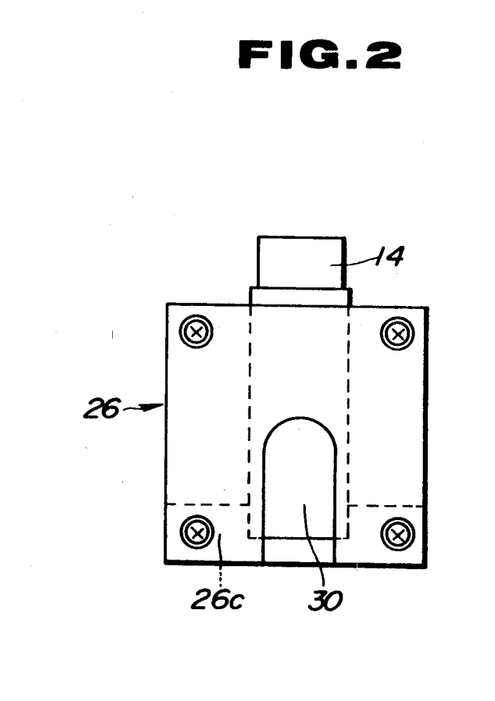
FIG. 2 is a side elevation of the first preferred embodiment of a cell holder of the instrument of FIG. 1.

The black box 10 houses a cell holder 26 which can move horizontally between locations beneath the cell port 12a and the injection opening 12b by means of a carrying mechanism which will be described hereafter. The location beneath the cell port 12a will be hereafter referred to as "the cell setting position", and the location beneath the injection opening will be hereafter referred to as "the injecting position". The cell holder 26 comprises a vessel made of a superior heat conductive metal such as copper, aluminium or the like. A through opening 26a is formed in the upper wall of the cell holder 26. The inner diameter of the through opening 26a is greater than the outer diameter of the cell 14, so that the cell 14 can be taken in and out the cell holder 26. The cell holder 26 houses a heater 26b and a temperature sensor not shown. The heater 26b is fixed to the inner side wall of the cell holder 26. Heat insulating material 28 is attached to the inner surface of the cell holder 26, so that the temperature in the cell 14 in which the sample and liquid reagent are injected can be kept to be constant. The cell 14 is vertically supported by a pan 26c installed on the bottom of the cell holder 26. As shown in FIG. 2, the pan 26c has an essentially U-shaped cross section, so that the light produced in the vicinity of the bottom of the cell can be detected.

As shown in FIG. 2, one of the side walls of the cell holder 26 defines an essentially U-shaped window 30 at the lower portion thereof, so that light produced by injecting the sample and reagent into the cell 14 can pass through the window 30 and be transmitted to the outside of the cell holder 26. The lowest portion of the window 30 is lower than the bottom of the cell 14, so that a very small amount of sample and reagent can be measured. According to the invention, a rectangular window may also be used as the window 30. The window 30 is covered with a protective cover 30a made of, for example, a glass, a polyethylene, a polystyrene or the like, which does not affect light passing trough the window 30. The protective cover 30a can also serve as a heat insulator. A spectroscopic filter which restricts a predetermined wavelength of light from passing therethrough may be substituted for the protective cover. By using such a spectroscopic filter, the quantity of a particular wavelength of light produced in the cell 14 can be measured.

The side wall 10b of the black box 10 has a through opening 32 at a location opposing the window 30 of the cell holder 26. The light receiving portion 34a of a photomultiplier tube 34 is inserted into the through opening 32 so that the light receiving surface 34b of the photomultiplier tube 34 opposes the window 30 of the black box 10, light transmitted from the cell 14 through the window 30 can be detected by means of the photomultiplier tube 34. The photomultiplier tube 34 is fixed to the side wall 10b of the black box 10 by means of a fixture 36. The light receiving portion 34a of the photomultiplier tube 34 is covered with a protective shutter 38 which can prevent light striking the light receiving surface 34b of the photomultiplier tube 34. Well known electric shutters may be used as the protective shutter 38. According to this embodiment of the invention, the electric shutter can automatically open or close on the basis of a pulse signal produced from the control unit. The shutter comprises a plurality of vanes 38a overlapping each other, such as a diaphragm, and a shutter mounting member 38b. The vanes 38a are made of plastic so as not to be corroded by the solvents used in producing chemiluminescent and bioluminescent phenomena. By closing the shutter 38, light can be blocked from impinging upon the light receiving surface.

Figure 3:
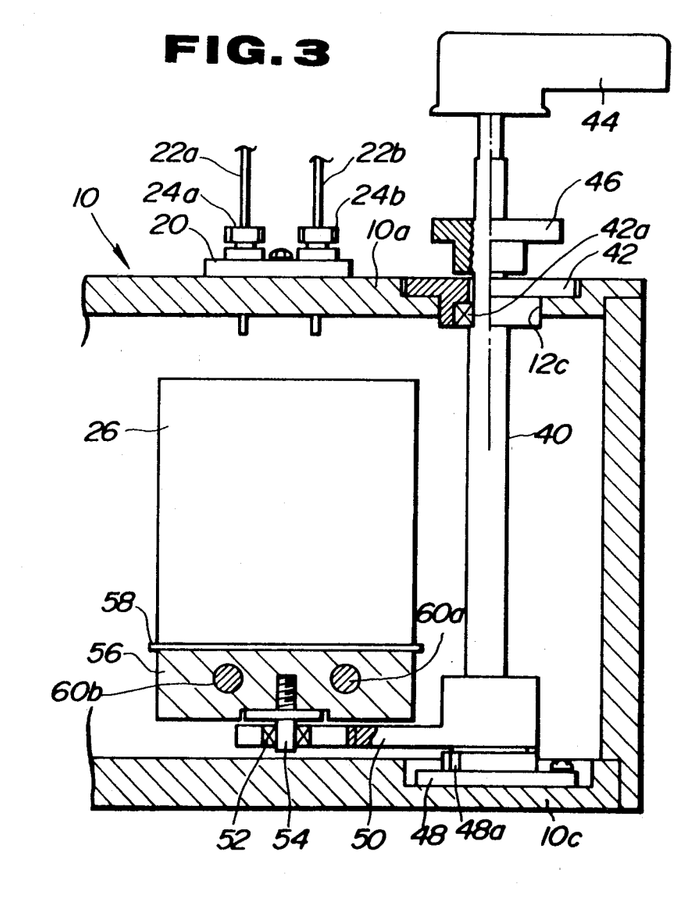
FIG. 3 is a section view of the instrument taken along the line III—III of FIG. 1.
Figure 4:
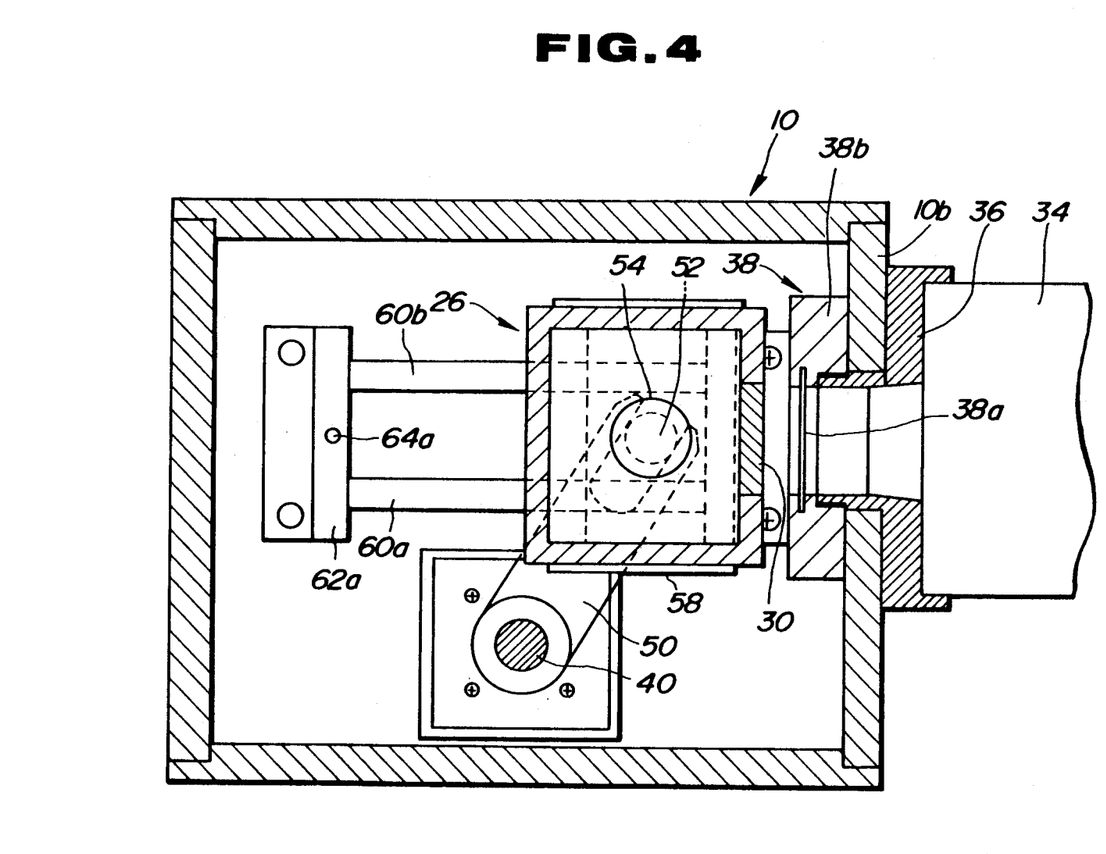
FIG. 4 is a section view of the instrument taken along the line IV—IV of FIG. 1.

FIGS. 3 and 4 are expanded cross sections taken along the line III—III and line IV—IV of FIG. 1, respectively. Making reference to FIGS. 3 and 4, the carrying mechanism of the cell holder 26 is described below.

As shown in FIG. 3, a rotary shaft 40 extends vertically and passes through the upper wall 10a. As seen clearly from FIG. 4, the rotary shaft 40 is disposed at a location between the cell port 12a and the injection opening 12b. The distance between the rotary shaft 40 and the cell port 12a is essentially equal to that between the rotary shaft 40 and the injection opening 12b. The upper portion of the rotary shaft 40 is pivotably supported by a bearing assembly 42 which inserted into an opening 12c of the upper plate 10a of the black box 10.

The bearing assembly 42 has a bearing 42a which is in contact with the rotary shaft 40. The upper end of the rotary shaft 40 is provided with a manually operable handle 44 for rotating the rotary shaft 40. A fixing member 46 engaging the rotary shaft 40 is provided between the bearing assembly 42 and the handle 44. When the fixing member 46 rotates clockwise, the fixing member 46 is thrusted against the bearing assembly 42, thereby fixing the rotary shaft 40.

The lower end of the rotary shaft 40 is pivotably supported by a bearing 48a of a bearing assembly 48 which is fixed to the bottom 10c of the black box 10. One end of a rotary arm 50 extending horizontally is fixed to the rotary shaft 40 in the vicinity of the lower end thereof. The other end of the rotary arm 50 pivotably supports a cylindrical roller 52 which has an opening at the center thereof. The opening of the roller 50 receives one end of a pin 54, and the other end of the pin 54 engages a cell holder sliding member 56 on which a cell holder mounting plate 58 is supported. The cell holder 26 is supported on the upper surface of the mounting plate 58.

As shown in FIG. 4, a pair of shafts 60a and 60b parallel to each other extends horizontally in the longitudinal direction between the cell setting position and the injecting position. As seen clearly from FIG. 1, the shafts 60a and 60b are supported by mounting brackets 62a and 62b having L-shaped cross section, so as to be separated from the bottom 10c by a predetermined distance. The mounting brackets 62a and 62b are fixed to the bottom 10c of the black box 10 by means of screws.

The cell holder sliding member 56 has two parallel tunnels which extend horizontally in the longitudinal direction. The shafts 60a and 60b pass through the tunnels so as to slidably support the cell holder sliding member 56. The cell holder sliding member 56 is provided with bearings not shown which are in contact with the shafts 60a and 60b, so as to allow it to slide smoothly on the shafts 60a and 60b between the cell setting position and the injecting position.

Vertically extending stoppers 64a and 64b are mounted on the upper ends of mounting brackets 62a and 62b. The stoppers 64a and 64b can extend or retract by means of springs provided therein. The stoppers 64a and 64b can engage recesses formed in the bottom(s) of the cell holder 26 and/or cell holder mounting plate 58. The stopper 64a engages one of the recesses when the cell holder 26 is positioned at the cell setting position beneath the cell port 12a, and the stopper 64b engages the other recess when the cell holder 26 is positioned at the injecting position beneath the injection opening 12b. The stoppers 64a and 64b are connected to detectors 66a and 66b, such as switches, sensors or the like. When the stopper 64a or 64b engages one of the recesses of the cell holder 26, the detectors 66a and 66b output detection signals to the control unit. In this manner, it is possible to detect that the cell 14 is accurately disposed at the injecting position. According to the invention, the respective mounting brackets 62a and 62b may have one or more stoppers.

When the cell holder sliding member 56 moves on the shafts 60a and 60b, operations of the rotary arm 50 and the roller 52 are described below.

The free end of the rotary arm 50 has an essentially U-shaped cut-out as expressed by a broken line in FIG. 4. The roller 52 is inserted into the U-shaped cut-out to be pivotably and slidably supported by the cut-out. That is, the roller 52 can slide in the cut-out in the longitudinal direction thereof while it rotates on its own axis. While the free end of the rotary arm 50 moves from the cell setting position to the intermediate location between the injecting and cell setting positions, the roller 52 moves in the cut-out in the direction of the rotary shaft 40 while it rotates on its own axis. Thereafter, when the free end of the rotary arm 50 moves from the intermediate location to the injecting position, the roller 52 moves in the cut-out in the opposite direction to the rotary shaft 40 while it rotates on its own axis.

Operation of the first preferred embodiment of an instrument for quantitative analysis, according to the invention, is described below.

First, the handle 44 is operated to rotate the rotary shaft 40 and the rotary arm 50 so that the cell holder sliding member 56, on which the cell holder 26 is supported, slides on the shafts 60a and 60b to reach the cell setting position. In this position, the cell holder sliding member 56 is stopped, and the stopper 64a engages the recess of the cell holder sliding member 56. As a result, the detector 66a outputs a signal to the control unit. In response to this signal, the control unit judges whether or not the protective shutter 38 is closed. If the protective shutter 38 is closed, the control unit outputs a pulse signal to the electromagnetic shutter 18, so that the shutter 18 opens.

The cell 14 is then introduced into the cell holder 26 through the cell port 12a by hand or by means of an auxiliary apparatus, such as a pincette, so as to be fixed to the pan 26c. Thereafter, the handle 44 is operated to rotate the rotary shaft 40 and the rotary arm 50, so that the cell holder 26 moves in the direction of the injecting position. When the cell holder 26 is seperated from the cell setting position, the detector 66a outputs a detector signal to the control unit. In response to this detector signal, the control unit outputs a pulse signal to the protective shutter 18, so that the shutter 18 is closed. When the cell holder 26 reaches the injecting position to be stopped, the stopper 64b engages the recess of the cell holder sliding member 56. As a result, the detector 66b detects that the cell holder 26 has reached the injecting position, and outputs a signal to the control unit. In response to the signal, the control unit judges whether or not the electromagnetic shutter 18 is closed. When the shutter 18 is closed, the control unit outputs a pulse signal to the protective shutter 38 so that the shutter 38 opens.

In this position, a sample to be tested and a reagent are injected into the cell 14 through the Teflon tubes 22a and 22b, respectively. Light produced by mixing of the sample with the reagent in the cell 14 passes through the window 30 and impinges upon the light receiving surface of the photomultiplier tube 34. The photomultiplier tube 34 detects the quantity of incident light.

When the cell 14 in the cell holder 26 is taken out the black box 10, the handle 44 is operated again to rotate the rotary arm 50 so that the cell holder 26, in which the cell 14 is housed, moves in the direction of the cell port 12a. When the cell holder 26 is separated from the injecting position, the detector 66b outputs a detector signal to the control unit. In response to this detector signal, the control unit outputs a pulse signal to the protective shutter 38, so that the shutter 38 is closed.

When the cell holder 26 reaches the cell setting position, the stopper 64a engages the recess of the cell holder sliding member 56, so that the detector 66a outputs a detector signal to the control unit. In response to this detector signal, the control unit judges whether or not the protective shutter 38 is closed. When the control unit determines that the protective shutter 38 is closed, it outputs a pulse signal to the electromagnetic shutter 18, so that the shutter 18 opens. Thereafter, the cell 14 is taken out the cell holder 26 by hand or by means of an auxiliary apparatus, such as a pincette.

DESCRIPTION OF THE SECOND PREFERRED EMBODIMENT

Figure 5:
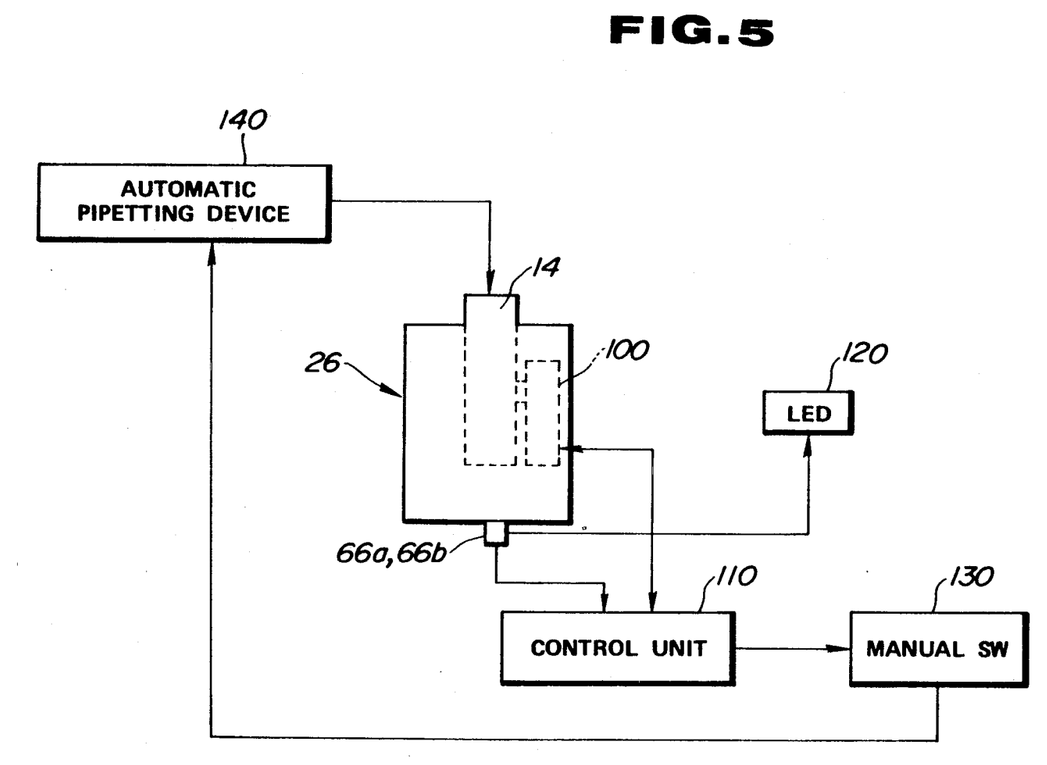
FIG. 5 is a block diagram of the second preferred embodiment of an instrument for quantitative analysis according to the present invention.
Figure 6:
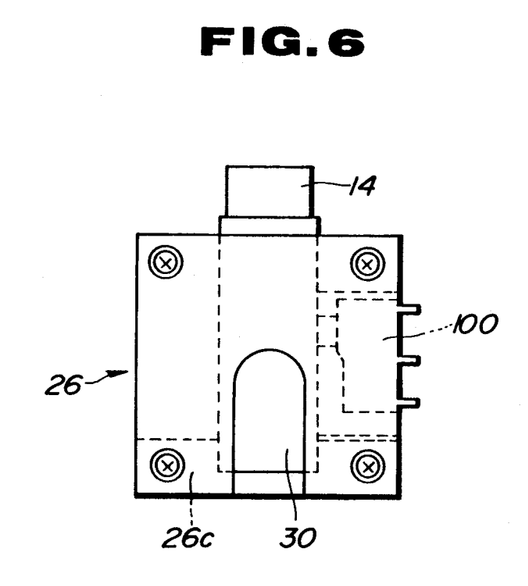
FIG. 6 is a side elevation of the second preferred embodiment of a cell holder of the instrument of FIG. 1.

FIG. 5 is a block diagram of the second preferred embodiment of an instrument for quantitative analysis according to the invention.

According to this embodiment, a cell detecting unit 100 such as a microswitch is mounted on the inner wall of the cell holder 26. The cell detecting unit 100 is electrically connected to a control unit 110 having a microcomputer, and a light emitting diode 120 which serves to indicate to the operator that the cell 14 is set in the cell holder 26. When the contact of the cell detecting unit 100 comes into contact with the cell 14, it is turned on to output a detector signal to the control unit 110 and the light emitting diode 120. A photoelectric switch, an ultrasonic switch, other type of a sensor which can detect the position of the cell 14 without coming into contact with the cell 14 may also be used as the cell detecting unit 100. The detectors 66a and 66b are electrically connected to the control unit 110 and the light emitting diode 120. The control unit 110 is also connected to a manually operable starter switch 130 installed outside the black box 10. When the cell detecting unit 100 is turned on and the stopper 64a or 64b engages the recess of the cell holder mounting plate 58, the system is made responsive to the starter switch 130 by means of the control unit 110. In this state, when the starter switch 130 is manually operated, the sample and/or the reagent are injected into the cell 14 by means of a automatic pipetting device 140. On the other hand, when the starter switch 130 is not active, the automatic pipetting device 140 is not operated if the starter switch is manually operated. In a similar manner to the first preferred embodiment, the control unit 110 can also control the electromagnetic shutter 18 and the protective shutter 38. The other mechanical aspects of the instrument are the same as that of the first preferred embodiment of the invention.

Operation of the second preferred embodiment of an instrument for quantitative analysis, according to the invention, is described below.

First, the handle 44 is operated to rotate the rotary shaft 40 and the rotary arm 50 so that the cell holder sliding member 56, on which the cell holder 26 is supported, slides on the shafts 60a and 60b to reach the cell setting position. In this position, the cell holder sliding member 56 is stopped, and the stopper 64a engages the recess of the cell holder sliding member 56. As a result, the detector 66a outputs a signal to the control unit 110. In response to this signal, the control unit 110 judges whether or not the protective shutter 38 is closed. When the protective shutter 38 is closed, the control unit 110 outputs a pulse signal to the electromagnetic shutter 18, so that the shutter 18 opens.

The cell 14 is then introduced into the cell holder 26 through the cell port 12a by hand or by means of an auxiliary apparatus, such as a pincette, so as to be fixed to the pan 26c. At this time, the cell detecting unit 100 is turned on to output a detector signal to the control unit 110. Thereafter, the handle 44 is operated to rotate the rotary shaft 40 and the rotary arm 50, so that the cell holder 26 moves in the direction of the injecting position. When the cell holder 26 reaches the injecting position, the stopper 64b engages the recess of the cell holder sliding member 56. As a result, the detector 66b detects that the cell holder 26 reaches the injecting position, and outputs a detector signal to the diode 120 so that the operator can recognize that the cell holder 26 is accurately positioned at the injecting position. At this time, the detector signal produced by the detector 66b is also outputted to the control unit 110. In response to the signal, the control unit 110 judges whether or not the electromagnetic shutter 18 is closed. If the shutter 18 is closed, the control unit outputs a pulse signal to the protective shutter 38 so that the shutter 38 opens.

In this case, since the both detector signals produced by the cell detecting unit 100 and the detector 66b are inputted to the control unit 110, the control unit 110 outputs a control signal to the starter switch 130, so that the starter switch 130 is in an active state. In this state, when the starter switch 130 is operated, the automatic pipetting device 140 is turned on, so that a sample to be tested and/or a reagent are injected into the cell 14 through the Teflon tubes 22a and 22b, respectively. Light produced by mixing of the sample with the reagent in the cell 14 passes through the window 30 and impinges upon the light receiving surface of the photomultiplier tube 34. The photomultiplier tube 34 detects the quantity of incident light.

While the present invention has been disclosed in terms of the preferred embodiment in order to facilitate better understanding of the invention, it should be appreciated that the invention can be embodied in various ways without departing from the principle of the invention. Therefore, the invention should be understood to include all possible embodiments and modifications to the shown embodiments which can be embodied without departing from the principle of the invention set out in the appended claims.

What is claimed is:

1. An instrument for detecting light produced in a reaction between first and second materials for performing quantitative analysis of said first material, which instrument comprises:

housing means for defining an optically sealable hollow chamber having an opening;

a cell holder, housed in said chamber, for supporting a cell therein, said cell holder being movable between a first position in which said cell is placed in and taken out of said cell holder through said opening of said housing means, and a second position in which said first material reacts with said second material;

carrying means for carrying said cell holder between said first and second positions wherein said carrying means comprises a horizontally extending member between said first and second position, said cell holder being slidable on said horizontally extending member in a longitudinal direction;

injection means for injecting said first and second materials into said cell when said cell holder is in said second position;

measuring means for measuring the quantity of light produced by the reaction between said first and second materials, said measuring means having a light passage and a light detecting means for detecting light passing through said light passage and impinging on said light detecting means;

first protective means, associated with said opening, for blocking light from being introduced into said housing means from the outside thereof, said first protective means being operable between an open position in which said first protective means fully opens said opening of the housing means in a first operation mode, and a closed position in which said first protective means fully closes said opening in a second operation mode;

second protective means, associated with said light passage of the measuring means, for blocking light from impinging on said light detecting means of the measuring means, said second protective means being operable between an open position in which said second protective means fully opens said light passage in said second operation mode, and a closed position in which said second protective means fully closes said light passage in said first operation mode;

cell holder detecting means for monitoring said cell holder for producing a first signal when said cell holder is disposed at said first position, and a second signal when said cell holder is disposed at said second position;

wherein said cell holder detecting means includes first and second switches, said first switch being turned on when a communication between said cell holder and said first switch is established in said first position, and said second switch being turned on when a communication between said cell holder and said second switch is established in said second position, said cell holder detecting means producing said first signal in response to turning ON of said first switch, and said second signal in response to turning ON of said second switch, and wherein aid first and second switches respectively are provided at the ends of said horizontally extending member, and wherein said first and second switches respectively project vertically from the ends of said horizontally extending member, and said cell holder has first and second recesses on the bottom thereof, said first and second switches being respectively engageable with said first and second recesses; and control means for receiving said signals produced by said cell holder detecting means for adjusting said first and second protective means such that said first and second protective means operate in said first operation mode when said control means receives said first signal, and in said second operation mode when said control means receives said second signal.

2. An instrument as set forth in claim 1, wherein said first and second switches respectively are turned on when said first and second switches engage said first and second recesses.

3. An instrument for detecting light produced in a reaction between first and second materials for performing quantitative analysis of said first material, which instrument comprises:

housing means for defining an optically sealable hollow chamber having an opening;

a cell holder, housed in said chamber, for supporting a cell therein, said cell holder being movable between a first position in which said cell is placed in and taken out of said cell holder through said opening of said housing means, and a second position in which said first material reacts with said second material;

carrying means for carrying said cell holder between said first and second positions wherein said carrying means comprises a horizontally extending member between said first and second position, said cell holder being slidable on said horizontally extending member in a longitudinal direction;

injection means for injecting said first and second materials into said cell when said cell holder is in said second position;

measuring means for measuring the quantity of light produced by the reaction between said first and second materials;

first detecting means for monitoring said cell holder for producing a first signal when said cell holder is disposed at said second position;

second detecting means for monitoring said cell for producing a second signal when said cell is housed in said cell holder at a predetermined position;

wherein said first detecting means includes a switching means which is turned on when the communication between said cell holder and said switching means is established in said second position, said first detecting means producing said first detector signal in response to turning ON of said switching means;

wherein said switching means projects vertically from the end of said horizontally extending member, and said cell holder has a recess on the bottom thereof, said switching means being engageable with said recess; and control means, associated with said injection means, for receiving said first and second signals and activating said injection means to inject said first and second materials into said cell.

4. An instrument as set forth in claim 3, wherein said switching means is turned on when said switching means engages said recess.

5. An instrument as set forth in claim 1, wherein said cell holder comprises a hollow vessel which has a first opening through which said cell is introduced into said cell holder, and a second opening through which light produced by the reaction between said first and second materials passes.

6. An instrument as set forth in claim 5, wherein said cell holder is provided with a pan which supports said cell and has a groove extending in the longitudinal direction, said groove fixing said cell to said pan and allowing light produced in the vicinity of the bottom of the cell to be measured by means of said measuring means.

7. An instrument as set forth in claim 6, wherein said cell holder is provided with means for holding temperature in the cell to be constant.

8. An instrument as set forth in claim 7, wherein said second opening is covered with a protective cover through which light produced by the reaction between said first and second materials can pass.

* * * * *